United States Patent [19]

Fisnerová et al.

[11] Patent Number: 4,599,415
[45] Date of Patent: Jul. 8, 1986

[54] 3-(2-(2-BENZIMIDAZOLYL) BENZOLYLOXYETHYL)-4(3H)-QUINAZOLINONE

[75] Inventors: Ludmila Fisnerová; Jaroslava Grimová; Zdenek Roubal; Oldrich Nemecek, all of Prague, Czechoslovakia

[73] Assignee: SPOFA, spojene podniky pro zdravotnickou vyrobu, Prague, Czechoslovakia

[21] Appl. No.: 720,744

[22] Filed: Apr. 8, 1985

[30] Foreign Application Priority Data

Apr. 6, 1984 [CS] Czechoslovakia ............... 2662-84

[51] Int. Cl.⁴ .......................................... C07D 403/12
[52] U.S. Cl. ..................... 544/284; 544/286; 548/330
[58] Field of Search ......................................... 544/284

[56] References Cited
U.S. PATENT DOCUMENTS 4,335,127  6/1982  Vandenberk et al. .............. 544/284

Primary Examiner—Glennon H. Hollrah
Assistant Examiner—James H. Turnipseed

[57] ABSTRACT

This invention relates to the compound 3-[2-(2-Benzimidazolyl) Benzoyloxyethyl]-4(3H)-Quinazolinone of Formula I, and a process for the preparation thereof. The compound exhibits strong analgesic activity and almost zero toxicity in laboratory mice.

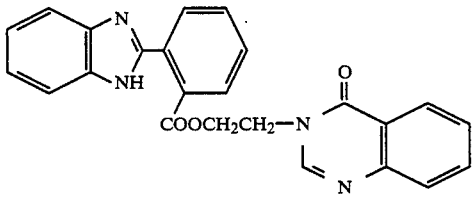

Formula I

The compound of Formula I is prepared by acylation of the compound 3-(2-hydroxyethyl)-4(3H)-quinazolinone with a reactive derivative of 2-(2-benzimidazolyl)benzoic acid, preferably its imidazolide, formed by treatment of the acid of Formula III with 1,1'-carbonyldiimidazole. The compounds of Formula II and Formula III are reacted in situ, at room temperature, and in the presence of an inert organic solvent. The product compound is isolated and purified by common techniques.

1 Claim, No Drawings

3-(2-(2-BENZIMIDAZOLYL) BENZOLYLOXYETHYL)-4(3H)-QUINAZOLINONE

This invention relates to the compound 3-[2-(2-Benzimidazolyl) Benzoyloxyethyl]-4(3H)-Quinazolinone of Formula I. and a process for the preparation thereof.

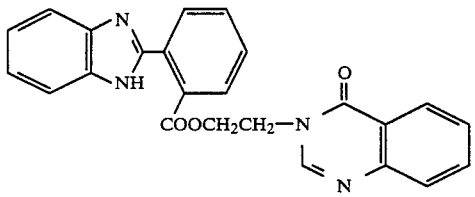

Formula I

BACKGROUND OF THE INVENTION

Analgesic compounds are known in the art, and among them the compound aminophenazone (1-phenyl-2,3-dimethyl-4-dimethylamino-5-pyrazolone) is particularly potent and nontoxic. The present compound, in a series of comparative assays with aminophenazone, demonstrated a surprising analgesic activity that is equal or superior to the activity of aminophenazone; and the new compound exhibits substantially no toxicity in laboratory mice.

SUMMARY OF THE INVENTION

In tests with laboratory mice, the analgesic activity of the new compound was $ED_{50}=115$ mg/kg upon oral adminisration. The activity of aminophenazone was $ED_{50}$ 32 104 mg/kg. The compound of Formula I also exhibited significant anti-inflamatory activity in laboratory rats at a dose ranging between 100–200 mg/kg, p.o. Most significantly, the new compound is almost completely nontoxic: its oral $LD_{50}$ was beyond experimental reach ($LD_{50}$ ⅛8 g/kg, p.o.). The combination of potent analgesic activity and extremely low toxicity provides for a unusually beneficial new compound.

The compound of Formula I is prepared by acylation of the compound 3-(2-hydroxyethyl)-4(3H)-quinazolinone of Formula II,

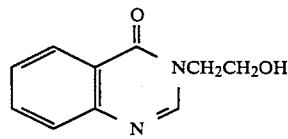

Formula II with a reactive derivative of 2-(2-benzimidazolyl)benzoic acid of Formula III.

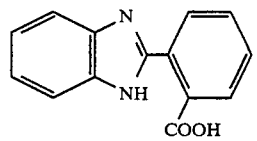

Formula III preferably its imidazolide, formed by treatment of the acid of Formula III with 1,1'-carbonyldiimidazole. These starting materials are known in the art and can be readily prepared according to the pertinent literature. The reaction between the compounds of Formula II and Formula III occurs in situ, at room temperature, and in the presence of an inert organic solvent, preferably a chlorinated alkane with 1 or 2 carbon atoms, such as dichloromethane. The liberated free imidazole is removed from the reaction mixture by a known method, such as washing with water. The desired product is then isolated by evaporation of the solvent and purified by crystallization.

Preferred Embodiment

The compound of Formula I can be prepared according to the following example. It will be understood by practicioners in the art that this example is illustrative, and does not narrow the scope of the appended claims The compound 1-1'-carbonyldiimidazole (17.1 g) is dissolved in 300 ml anhydrous dichloromethane at 20°–30°C. Then, 25.2 g of 2-(2-benzimidazolyl)-benzoic acid is added and the mixture is stirred until dissolution of the solid. The mixture is then treated with 20 g of 3-(2-hydroxyethyl)-4(3H)-quinazolinone. Stirring is continued at the same temperature for 6 hours, is left standing overnight, and is stirred for an additional 8 hours. The resulting solution is washed with water, evaporated to dryness under reduced pressure and the residue is crystallized from 2-propanol to give 30 g (70% of theoretical yield) of the title compound, with a melting point of 192°–193° C.

We claim:

1. 3-[2-(2-Benzimidazolyl) Benzoyloxyethyl]-4(3H)-Quinazolinone of the formula

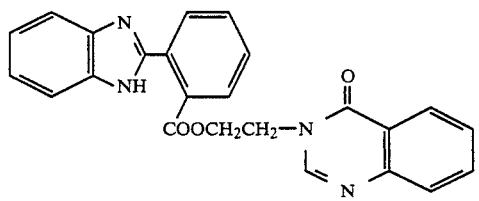

* * * * *